(12) United States Patent
Gann et al.

(10) Patent No.: US 10,293,073 B2
(45) Date of Patent: May 21, 2019

(54) MOISTURE MANAGEMENT FOR WOUND CARE

(71) Applicant: Avent, Inc., Alpharetta, GA (US)

(72) Inventors: John P. Gann, Portland, OR (US); Dave A. Soerens, Neenah, WI (US)

(73) Assignee: Avent, Inc., Alpharetta, GA (US)

( * ) Notice: Subject to any disclaimer, the term of this patent is extended or adjusted under 35 U.S.C. 154(b) by 74 days.

(21) Appl. No.: 15/506,054

(22) PCT Filed: Aug. 20, 2015

(86) PCT No.: PCT/US2015/046017
§ 371 (c)(1),
(2) Date: Feb. 23, 2017

(87) PCT Pub. No.: WO2016/032833
PCT Pub. Date: Mar. 3, 2016

(65) Prior Publication Data
US 2018/0214597 A1    Aug. 2, 2018

Related U.S. Application Data

(60) Provisional application No. 62/043,476, filed on Aug. 29, 2014.

(51) Int. Cl.
*A61L 15/38* (2006.01)
*A61L 15/40* (2006.01)
(Continued)

(52) U.S. Cl.
CPC ............ *A61L 15/38* (2013.01); *A61L 15/40* (2013.01); *A61L 15/425* (2013.01); *A61L 15/46* (2013.01);
(Continued)

(58) Field of Classification Search
CPC .......... A61L 15/38; A61L 15/60; A61L 15/46; A61L 15/425; A61L 15/40;
(Continued)

(56) References Cited

U.S. PATENT DOCUMENTS 3,338,992 A    8/1967 Kinney
3,341,394 A    9/1967 Kinney
(Continued)

FOREIGN PATENT DOCUMENTS

| EP | 2 774 629 A2 | 9/2014 |
|---|---|---|
| WO | WO 02/45761 A1 | 6/2002 |
| WO | WO 2011/058311 A1 | 5/2011 |

OTHER PUBLICATIONS

Basketter et al., "Patch tests versus use tests in skin irritation risk assessment", Contact Dermatitis, vol. 39, No. 5, Nov. 1998, Abstract, 1 page.
(Continued)

*Primary Examiner* — Robert A Wax
*Assistant Examiner* — Quanglong N Truong
(74) *Attorney, Agent, or Firm* — Dority & Manning, P.A.

(57) ABSTRACT

There is provided an absorbent system for wound care products having a liquid-absorbing, wound-contacting, lower layer and a more highly absorbent upper layer in liquid communication with said lower layer. Liquid communication may be provided by pores running between the layers. The dressing may include antimicrobial agents, agents to promote healing and other functional agents.

15 Claims, 3 Drawing Sheets

(51) Int. Cl.
*A61L 15/42* (2006.01)
*A61L 15/46* (2006.01)
*A61L 15/60* (2006.01)

(52) U.S. Cl.
CPC .......... *A61L 15/60* (2013.01); *A61L 2300/104* (2013.01); *A61L 2300/114* (2013.01); *A61L 2300/202* (2013.01); *A61L 2300/208* (2013.01); *A61L 2300/406* (2013.01); *A61L 2300/414* (2013.01); *A61L 2300/428* (2013.01); *A61L 2300/434* (2013.01)

(58) Field of Classification Search
CPC .......... A61L 2300/202; A61L 2300/428; A61L 2300/104; A61L 2300/114; A61L 2300/414; A61L 2300/406; A61L 2300/208; A61L 2300/434
See application file for complete search history.

(56) References Cited

U.S. PATENT DOCUMENTS

| | | | |
|---|---|---|---|
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 4,100,324 A | 7/1978 | Anderson et al. | |
| 4,340,563 A | 7/1982 | Appel et al. | |
| 4,818,464 A | 4/1989 | Lau | |
| 5,057,368 A | 10/1991 | Largman et al. | |
| 5,069,970 A | 12/1991 | Largman et al. | |
| 5,277,976 A | 1/1994 | Hogle et al. | |
| 5,466,410 A | 11/1995 | Hills | |
| 5,935,682 A * | 8/1999 | Wallstrom | A61F 13/15707 428/138 |
| 6,596,402 B2 | 7/2003 | Soerens et al. | |
| 7,014,630 B2 | 3/2006 | Rosati | |
| 7,762,045 B2 | 7/2010 | Rosati | |
| 7,813,807 B2 | 10/2010 | Franklin | |
| 8,075,537 B2 | 12/2011 | Franklin et al. | |
| 8,166,731 B2 | 5/2012 | Rosati | |
| 8,900,209 B2 | 12/2014 | Rosati | |
| 2004/0132377 A1* | 7/2004 | Fujikawa | A61F 13/539 442/389 |
| 2005/0251084 A1 | 11/2005 | Rosati | |
| 2006/0200100 A1 | 9/2006 | Rosati | |
| 2008/0021373 A1 | 1/2008 | Rosati | |
| 2010/0038280 A1 | 2/2010 | Franklin et al. | |
| 2010/0041998 A1 | 2/2010 | Postel | |
| 2010/0063462 A1 | 3/2010 | Postel et al. | |
| 2010/0087946 A1 | 4/2010 | Postel et al. | |
| 2011/0111012 A1* | 5/2011 | Pepper | A61F 13/00995 424/445 |
| 2011/0208101 A1* | 8/2011 | Keller | A61F 13/00017 602/44 |
| 2011/0257610 A1 | 10/2011 | Franklin | |
| 2011/0257617 A1 | 10/2011 | Franklin | |
| 2011/0282259 A1 | 11/2011 | Postel et al. | |
| 2012/0059301 A1 | 3/2012 | Franklin | |
| 2013/0060216 A1 | 3/2013 | Junginger et al. | |
| 2013/0296630 A1 | 11/2013 | Franklin | |

OTHER PUBLICATIONS

Cutting, Keith, "Avoidance and management of peri-wound maceration of the skin", Professional Nurse, vol. 18, No. 1, Sep. 2002, 4 pages.
Winter, George D., "Formation of the Scab and the Rate of Epithelization of Superficial Wounds in the Skin of the Young Domestic Pig", Nature, vol. 193, Jan. 1962, Abstract, 1 page.
International Search Report and Written Opinion for PCT/US2015/046017, dated Oct. 23, 2015, 11 pages.

* cited by examiner

MOISTURE MANAGEMENT FOR WOUND CARE

RELATED APPLICATIONS

The present application is the national stage entry of International Patent Application No. PCT/US2015/046017 having a filing date of Aug. 20, 2015, which claims priority to U.S. Provisional Application Ser. No. 62/043,476, filed on Aug. 29, 2014, both of which are incorporated herein in their entirety by reference thereto.

BACKGROUND

Moisture management is critical to optimal wound healing. In 1962, George Winter first introduced the concept of occlusive wound dressings where he observed that the moisture promoted by polyethylene coverings enhanced the rate of epitheliazation versus the unoccluded wounds which were dry. (Winter, G. D., *Formation of the Scab and the Rate of Epithelization of Superficial Wounds in the Skin of the Young Domestic Pig*, Nature, 193, 293-294.)

Moist wounds tend to heal at a faster rate and leave less scarring than dry wounds. In addition, numerous controlled studies have established that a moist wound environment can facilitate cellular growth and collagen proliferation, whereas dry wound tissue can be more prone to infection, scarring, delayed healing and pain. More specifically, moisture can promote wound healing by increasing the concentration of lipid mediators, cytokines, and growth factors, which are typically present in wound fluid. Moist wounds can also reduce scab formation which permits cellular migration over the wound bed.

Excessive moisture on the other hand, is also not ideal for wound healing. For example, excessive moisture can harbor bacteria and other microbes that increase the bio-burden of the wound. In addition, wound moisture can contain cellular debris and enzymes that can irritate the wound bed and delay healing. More specifically, one issue surrounding excess wound moisture is maceration, especially of the periwound area. Maceration can be defined as the over hydration of tissue, for example, around the wound bed, due to the retention of excess moisture. (Cutting, et. al., *Avoidance and Management of Peri-Wound Maceration of the Skin*, Nursing Times, September 2002). Thus, maceration can cause the inhibition of cell proliferation, inflammation, and ultimately longer healing times. In addition, it has been shown by Basketter D., Gilpin G., Kuhn M., Lawrence D., Reynolds F., and Whittle E. in *Patch Tests Versus Use Tests In Skin Irritation Risk Assessment*, Contact Dermatitis 1998; 39(5): 252-6, that macerated skin can be more sensitive to irritants.

There is a variety of wound care devices designed to address the issues of optimal wound moisture. For dry wounds, there are transparent occlusive dressings which act to retain moisture, hydrocolloids which also act to retain moisture, and hydrogels which contain a large amount of water that helps to moisten the wound. The problem with these approaches, however, is that they can contribute too much moisture. For wounds with heavy exudate, there are a variety of foams, alginates, and absorbent materials that are designed to simply soak up wound fluid. The issue with these approaches is that once the moisture is absorbed by the wound dressing it is simply held in place next to the wound, where it can still result in maceration as the patient's body reabsorbs the exudate.

Thus, a system in which a wound dressing would channel or direct excess moisture away from the patient, while maintaining some moisture near the wound to prevent desiccation of the wound would be welcomed in the art. Therefore, it is an object of the present disclosure to provide a wound dressing that can transport liquid exudate to remote storage locations.

SUMMARY

Aspects and advantages of the invention will be set forth in part in the following description, or may be obvious from the description, or may be learned through practice of the invention.

In one aspect, the present disclosure is directed to an absorbent system that includes components that have been designed, arranged, and assembled so that some liquid exudate from a wound is moved away from the wound to remote storage. While the excess liquid is stored remotely, it is desired that sufficient liquid remains in proximity to the wound so that the wound heals faster and with less scarring. More specifically, the present disclosure is directed to a wound dressing for a wound of a patient. The wound dressing includes a wound-contacting lower layer having a first liquid absorption rate and an upper layer configured adjacent to the lower layer. The upper layer is in liquid communication with the lower layer. Further, the upper layer has a second liquid absorption rate that is higher than the first liquid absorption rate.

In one embodiment, the lower layer includes a superabsorbent polymer having a high degree of crosslinking. In further embodiments, the upper layer may include a superabsorbent with a lower degree of crosslinking than the lower layer. More specifically, in certain embodiments, the superabsorbent of the upper layer may be dispersed in a hydrogel.

In another embodiment, the liquid communication between the layers is provided by one or more perforations configured in at least one of the lower layer or the upper layer. More specifically, in certain embodiments, the one or more perforations are configured in the lower layer and the upper layer. In addition, the one or more perforations may include at least one pores, channels, slits, holes, or similar. In alternative embodiments, the liquid communication between the layers may be provided by physical contact between the layers.

In additional embodiments, the upper layer may include an absorbent foam. For example, in certain embodiments, the foam may include a liquid absorption rate that is higher than the first liquid absorption rate the lower layer.

In yet another embodiment, at least one of the lower layer or the upper layer may include one or more additives. For example, in certain embodiments, the one or more additives comprise at least one of silver salts, silver nanoparticles, silver sulfadiazine, bacitracin, neomycin, polymyxin b, sulfacetamide sodium, sulfur, quaternary ammonium compounds, povidone iodine, or similar.

In further embodiments, at least one of the lower layer or the upper layer may include agents to promote wound healing such as oxygen, nitrogen oxide, growth factors, vitamin C, vitamin E, aloe, or combinations thereof. In addition, at least one of the lower layer or the upper layer further comprises debriding agents such as papain, honey, trypsin, collagenase, urea, or combinations thereof.

In another aspect, the present disclosure is directed to a wound dressing for covering a wound of a patient. The wound dressing includes a wound-contacting lower layer having a first liquid absorption rate and an upper layer configured adjacent to the lower layer and facing away from the patient. Further, the upper layer is in liquid communication with the lower layer via one or more perforations configured in the lower layer and the upper layer. In addition, the upper layer has a second liquid absorption rate that is higher than the first liquid absorption rate. It should also be understood that the wound dressing may further include any of the additional features as described herein.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art is set forth in the specification, which makes reference to the appended figures, in which.

DEFINITIONS

"Hydrophilic" as used herein generally describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials can be provided by a Cahn SFA-222 Surface Force Analyzer System, or a substantially equivalent system. When measured with this system, fibers having contact angles less than 90° are designated "wettable" or hydrophilic, while fibers having contact angles equal to or greater than 90° are designated "nonwettable" or hydrophobic.

"Liquid communication" as used herein generally means that liquid, such as wound exudate, can travel from one location to another location.

"Particles" as used herein generally refers to any geometric form such as, but not limited to, spherical grains, cylindrical fibers or strands, or the like.

"Spunbonded fibers" as used herein generally refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Rather, spunbond fibers are generally continuous and have average diameters (from a sample of at least 10) larger than 7 microns, more particularly, between about 10 and 20 microns. The fibers may also have shapes such as those described in U.S. Pat. No. 5,277,976 to Hogle et al., U.S. Pat. No. 5,466,410 to Hills and U.S. Pat. Nos. 5,069,970 and 5,057,368 to Largman et al., which describe fibers with unconventional shapes.

"Meltblown fibers" as used herein generally means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241. Meltblown fibers are microfibers which may be continuous or discontinuous and are generally smaller than 10 microns in average diameter. In addition, meltblown fibers are generally tacky when deposited onto a collecting surface.

As used herein, the term "coform" means a process in which at least one meltblown diehead is arranged near a chute through which other materials are added to the web while it is forming. Such other materials, for example, may be pulp, superabsorbent particles, natural or synthetic staple fibers, or similar. Coform processes are shown in commonly assigned U.S. Pat. No. 4,818,464 to Lau and U.S. Pat. No. 4,100,324 to Anderson et al. Webs produced by the coform process are generally referred to as coform materials.

"Bonded carded web" as used herein generally refers to webs that are made from staple fibers which are sent through a combing or carding unit, which separates and aligns the staple fibers in the machine direction to form a generally machine direction-oriented fibrous nonwoven web. Such fibers (which typically come in bales) can be placed in an opener/blender or picker which separates the fibers prior to the carding unit. Once the web is formed, the web is then bonded by one or more of several known bonding methods. For example, one such bonding method may include powder bonding, wherein a powdered adhesive is distributed through the web and then activated, usually by heating the web and adhesive with hot air. Another suitable bonding method may include pattern bonding, wherein heated calender rolls or ultrasonic bonding equipment are used to bond the fibers together, usually in a localized bond pattern, though the web can be bonded across its entire surface if so desired. Another suitable and well-known bonding method, particularly when using conjugate staple fibers, may also include through-air bonding.

"Airlaying" as used herein generally refers to a well-known process by which a fibrous nonwoven layer can be formed. In the airlaying process, bundles of small fibers having typical lengths ranging from about 3 millimeters (mm) to about 19 mm are separated and entrained in an air supply and then deposited onto a forming screen, usually with the assistance of a vacuum supply. The randomly deposited fibers then are bonded to one another using, for example, hot air or a spray adhesive.

TEST METHOD

Absorption Time Index (ATI):

In this test, the absorbent capacity of a superabsorbent material is determined versus time for up to 200 minutes under light pressure, e.g., about 0.01 psi.

A one inch (25.4 mm) inside diameter cylinder with an integral 100 mesh stainless steel screen on one end is used to hold 0.16±0.005 grams of dry superabsorbent. The superabsorbent should be carefully placed in the cylinder such that the superabsorbent does not stick to the sides of the cylinder. The cylinder should be tapped gently to more evenly distribute the superabsorbent on the screen. A 4.4 gram, 0.995-inch diameter plastic piston is then placed in the cylinder and the cylinder, piston and superabsorbent assembly weighed. The assembly is placed in a 3 inch by 3 inch (76.4 mm by 76.4 mm) fluid basin having a 0.875 weight percent NaCl saline solution to a depth of 1 centimeter (cm). Tap the cylinder gently to remove any air trapped under it and maintain the saline solution depth at about 1 cm throughout the test.

Use a timer capable of reading 200 minutes in one second intervals. Start the timer. After 5 minutes in the solution, remove the assembly and blot the assembly on absorbent paper. A preferred paper may include KLEENEX® Premium Dinner Napkins from Kimberly-Clark Corp. although any other effective paper may be used. In blotting, the paper should be pressed tightly against the cylinder to ensure good contact. For example, the cylinder may be touched to dry paper three times and the paper checked after the third time, with very little liquid removed the third time. The assembly can then be weighed and returned to the fluid basin. Blotting and weighing the assembly can take about 5 seconds and the timer should be kept running throughout the test. Readings should be taken at 5, 10, 15, 30, 45, 60, 75, 90, 120, 160 and 200 minutes, with fresh dry napkins used for blotting for each reading.

After the final reading, the grams of fluid absorbed per gram of superabsorbent can be calculated. Thus, the amount of liquid absorbed at particular times divided by the amount absorbed at 200 minutes may be plotted versus time for a graphical representation of the absorption rate.

The Absorption Time Index (ATI) can be calculated as follows:

$$ATI=(t_{10}+t_{20}+t_{30}+t_{40}+t_{50}+t_{60}+t_{70}+t_{80}+t_{90})/9$$

where $t_n$ represents the time in minutes at which n percentage of the absorbent capacity at 200 minutes is used, e.g. $t_{30}$ is the time at which 30 percent of the total capacity is used.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention include such modifications and variations as come within the scope of the appended claims and their equivalents.

Generally, the present disclosure is directed to a wound dressing that utilizes different absorptive capacities of superabsorbent polymers in a layered configuration, in conjunction with the wicking ability of hydrophilic surfaces, in order to channel excess moisture away from the patient, while maintaining some moisture to prevent desiccation of the wound.

In practice, the layer that contacts the wound (the lower layer) is desirably a material with low or moderate liquid absorption capacity, for example, certain superabsorbent polymers. Such properties allow the dressing to absorb some moisture. In addition, the lower layer can be held adjacent to the wound bed such that the wound will not desiccate. The upper layer of the wound dressing may include a material with a higher absorption capacity than the lower layer, such as, for example, a superabsorbent with a low degree of crosslinking, polyurethane foam, or any other suitable material that allows for greater absorption of liquid than the lower, wound-contacting layer. Further, the lower and upper layers are in liquid communication with each other. For example, in certain embodiments, the wound dressing may include channels or pores configured therein that allow wound exudate to travel from the wound bed through the lower, less absorbing layer and into the layer with the higher absorption capacity. Once in the upper layer the moisture is essentially sequestered where it cannot cause wound maceration.

In certain embodiments, the absorption capacities of the wound dressing of the present disclosure can be tailored by manipulation of the crosslink density of a superabsorbent since the absorption capacity is inversely proportional to crosslink density. For example, the lower layer of the dressing may have a high amount of crosslinking, whereas the upper layer may have less crosslinking to allow for more moisture absorption capacity. In particular embodiments, both layers may absorb moisture but the upper layer may absorb more.

In additional embodiments, the absorption capacities of the wound dressing of the present disclosure can be tailored by choice of polymers in the upper and lower layers such that the upper layer has a high absorption capacity and the lower layer has a lower moisture absorption capacity. For example, in certain embodiments, the lower layer may be constructed of a non-ionic polyacrylamide or polyurethane, whereas the upper layer may be constructed of a highly absorbing sodium polyacrylate or polyacrylamide/polyacrylate copolymer.

In particular embodiments, the morphology of the wound contact layer can be that of a solid, flexible polymer sheet, or flexible closed cell foam. More specifically, in certain embodiments, the upper layer may include a solid flexible polymer sheet.

The upper and lower layers may be held together using any suitable means. For example, in certain embodiments, the upper and lower layers may be held together by an adhesive, by choosing materials that are inherently tacky, or by choosing the upper and lower layers from materials that have an affinity for one another such as is the case with polyacrylamide and carboxymethylcellulose. Further, the layers may also be held together by mechanical means such as by the punching of the pores, slots or channels through the layers, resulting in entanglement of the interfaces of the layers. The upper and lower layers may also be held together by coating one layer in liquid form onto another layer that is in solid form. The coating could be applied to the substrate layer by slot coating, Meyer rod, or similar technique familiar to those skilled in coating technologies.

In certain embodiments, liquid communication between the layers provides improved functioning of the wound dressing. For example, the pores, slots, or fluid wicking channels can be useful in liquid communication since, without these structures, the fluid must diffuse though the lower, less absorbent layer where only then can the fluid be absorbed by the upper layer. In certain embodiments, the fluid wicking channels can be, for example, circular-shaped holes formed into the lower layer and/or the upper layer using a punch-type die or any other suitable cutting device. In further embodiments, the pores or slots may include sides that are close enough to each other to allow for wicking and/or capillary action. The pores or channels may also be cast into the polymer when it is made, for example, as in a molding process. In particular embodiments, the pore density can range from about 1 per square inch to about 25 per square inch (1 to 4 per square cm).

The wound-contact layer (i.e. the lower layer) may contain additives of various functional natures designed to promote wound healing. Such additives may include antimicrobials such as silver salts, silver nanoparticles, silver sulfadiazine, bacitracin, neomycin, polymyxin b, sulfacetamide sodium, sulfur, quaternary ammonium compounds, povidone iodine, or similar agents known to those skilled in the art. It can also contain agents to promote wound healing such as oxygen, nitrogen oxide, growth factors, vitamin C, vitamin E, aloe, or similar. Debriding agents such as papain, honey, trypsin, collagenase, urea, or similar can also be used. The aforementioned additives can be used alone or in conjunction with each other provided there are no interaction issues.

Figure 1:
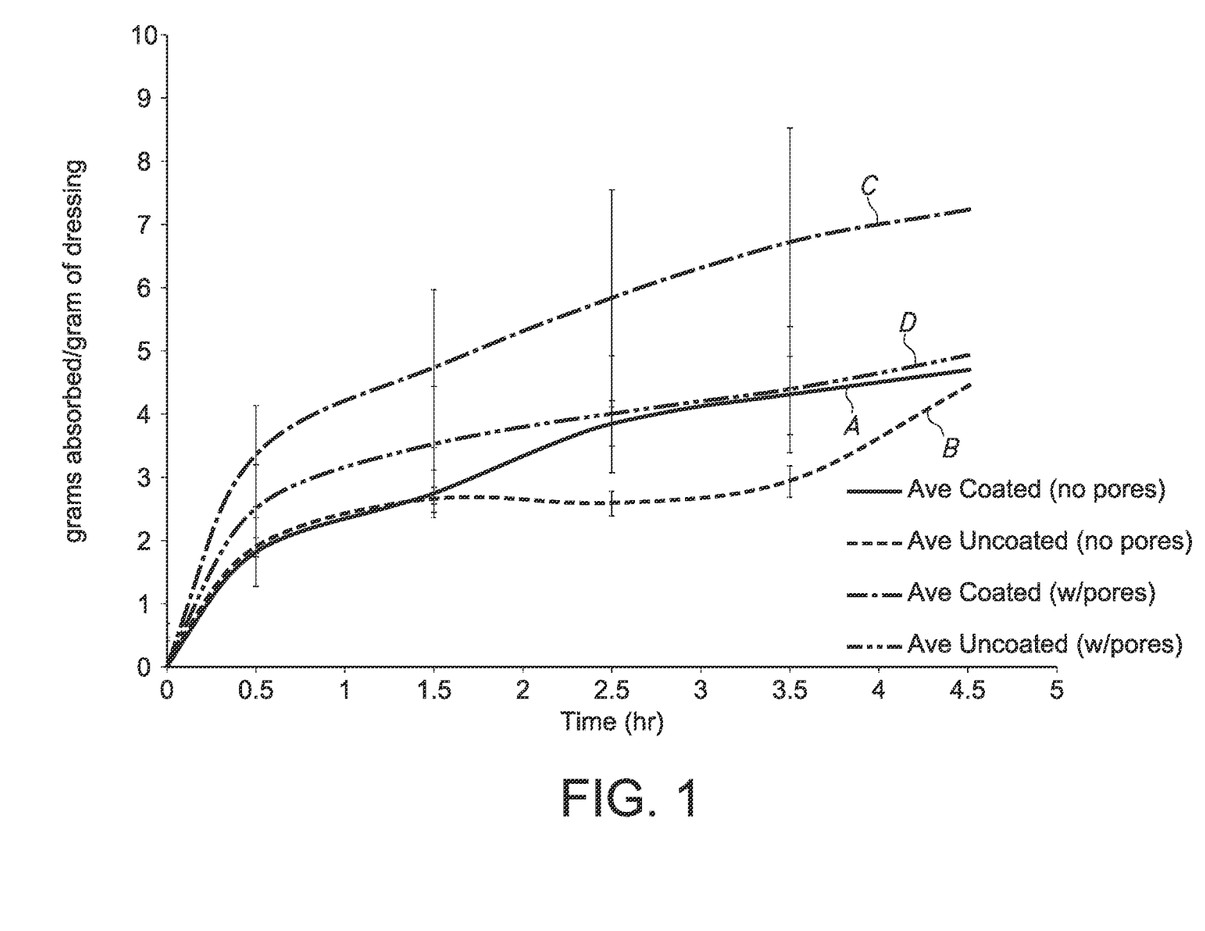
FIG. 1 illustrates one embodiment of a graph of grams of fluid absorbed per gram of dressing (y-axis) versus time in hours (x-axis) for various configurations of wound dressings according to the pressure disclosure.

Referring now to FIG. 1, one embodiment of a graph of grams of fluid absorbed per gram of dressing (y-axis) versus time in hours (x-axis) for various configurations of wound dressings according to the present disclosure is illustrated. In one sample, as shown, a highly absorbing layer of superabsorbent was coated onto a polyacrylamide based substrate. Further as shown, line A demonstrates a minimal difference in the absorption rate of saline when compared to the polyacrylamide substrate alone (i.e., not coated with highly absorbing superabsorbent) when no channels were created in the lower layer (line B) for up to 1.5 hours after first contact with the saline solution. In addition, the samples with the pore structures added (line C (coated); line D (uncoated)) illustrates a faster absorption rate as well as an overall higher absorption capacity, indicating that the wicking of the liquid into the upper layer is essential for efficient removal of excess exudate from the wound bed. The various samples were tested by placing them in Petree dishes with 20 mls of 0.9% saline. Red food coloring was added as a contrast agent. After certain time periods, the samples were removed from the Petree dishes, dabbed with a paper towel to remove visible excess fluid, and then weighed. This was carried out up to 4.5 hours to monitor the rate or fluid absorption.

Additional examples were developed to test various superabsorbents in relation to the wound contacting layer. All of the structures were given pores, which resulted in good movement of the liquid into the upper layer. There were no major differences between the structures based on the type of superabsorbent as all example materials with pores performed comparably. These examples are below.

EXAMPLES

Example 1—Cast Lower Layer, Coated Upper Layer, with Pores

For Example 1, the lower layer of the wound dressing is composed of a non-ionic crosslinked polyacrylamide at approximately 45% wt/wt basis blended with glycerin also at approximately 45% wt/wt, as well as about 5% guar gum and approximately 5% of excipients. The lower layer is prepared by casting the polymer blend as sheets and then cutting to the approximate size of 4 inches by 4 inches (10 cm by 10 cm) and approximately 0.5 cm thickness. This lower layer is hydrophilic and capable of absorbing water.

An upper, more absorbent layer is added by the method described in U.S. Pat. No. 6,596,402 B2, wherein a water-soluble base polymer is coated onto the lower layer of the wound dressing. As this layer dries, the upper layer leaves a resulting cross-linked polyethyleneoxide hydrogel coating that was capable of absorbing approximately 20 times its weight in water. The layered dressing was then perforated using a punch type die such that multiple "pores" are formed through the two layers, each pore of about 0.5 mm to 1 mm in diameter at a pore density of 3 per square inch (approximately 1 per square cm).

Figure 2:
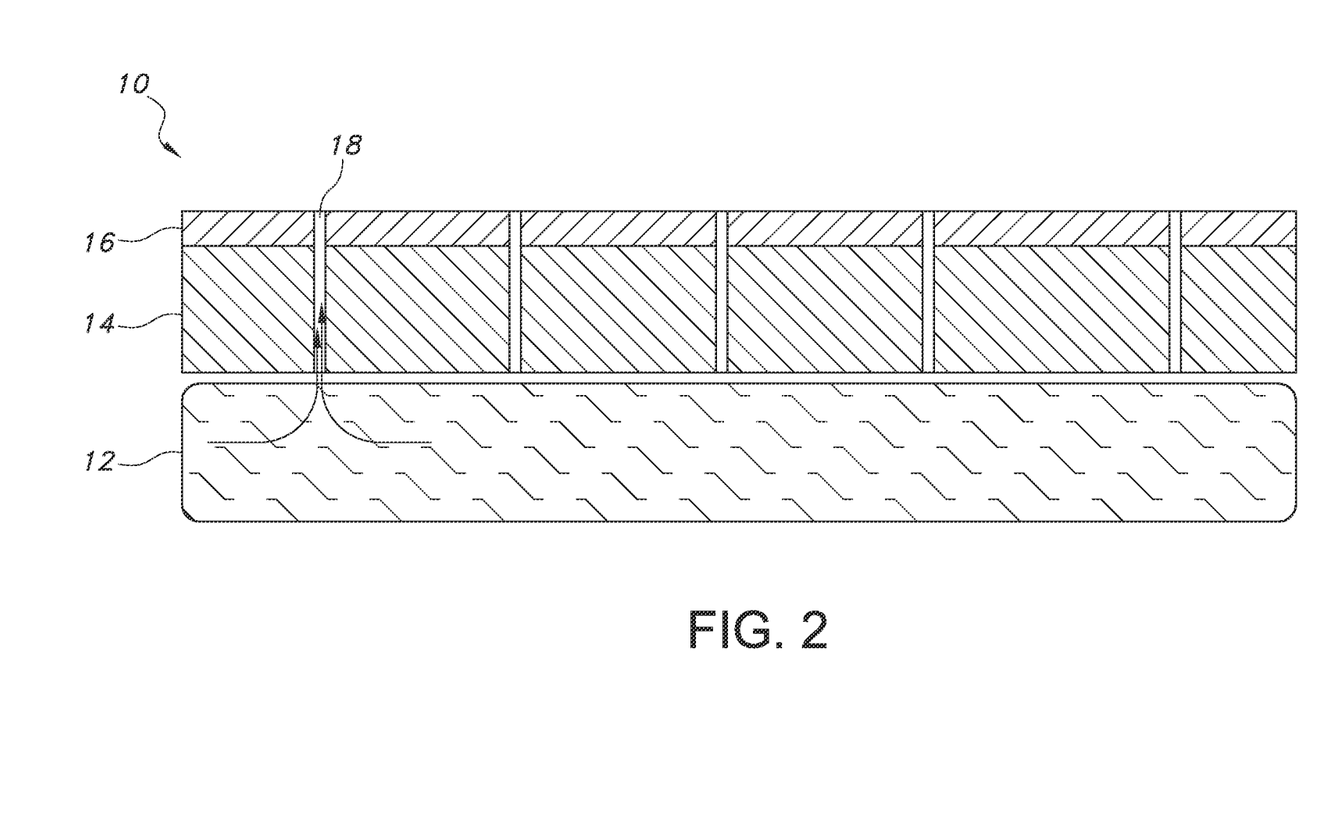
FIG. 2 illustrates a schematic cross-sectional view of one embodiment of a dressing construction according to the present disclosure, particularly illustrating a dressing with two layers having pores configured therein to assist with liquid movement through the layers, wherein the lower layer is in contact with the wound and the upper layer is in liquid communication with the lower layer, and wherein the upper layer is a water-soluble polymer mixture coated onto the lower layer of the dressing.

As a variation, the amount of material used in the upper layer can be adjusted to allow for more or less moisture holding capacity as desired, but in this embodiment the weight of the upper layer was from about 25% to about 35% of the overall weight of the sample. A schematic cross-sectional drawing of this construction is shown in FIG. 2, wherein the wound dressing 10 is placed on the wound 12. As shown, the wound dressing 10 has two layers, with the lower layer 14 being in contact with the wound 12 and the upper layer 16 being configured away from a user. In addition, as shown, the wound dressing 10 includes a plurality of pores 18 configured through the layers, 14, 16.

Example 2

Figure 3:
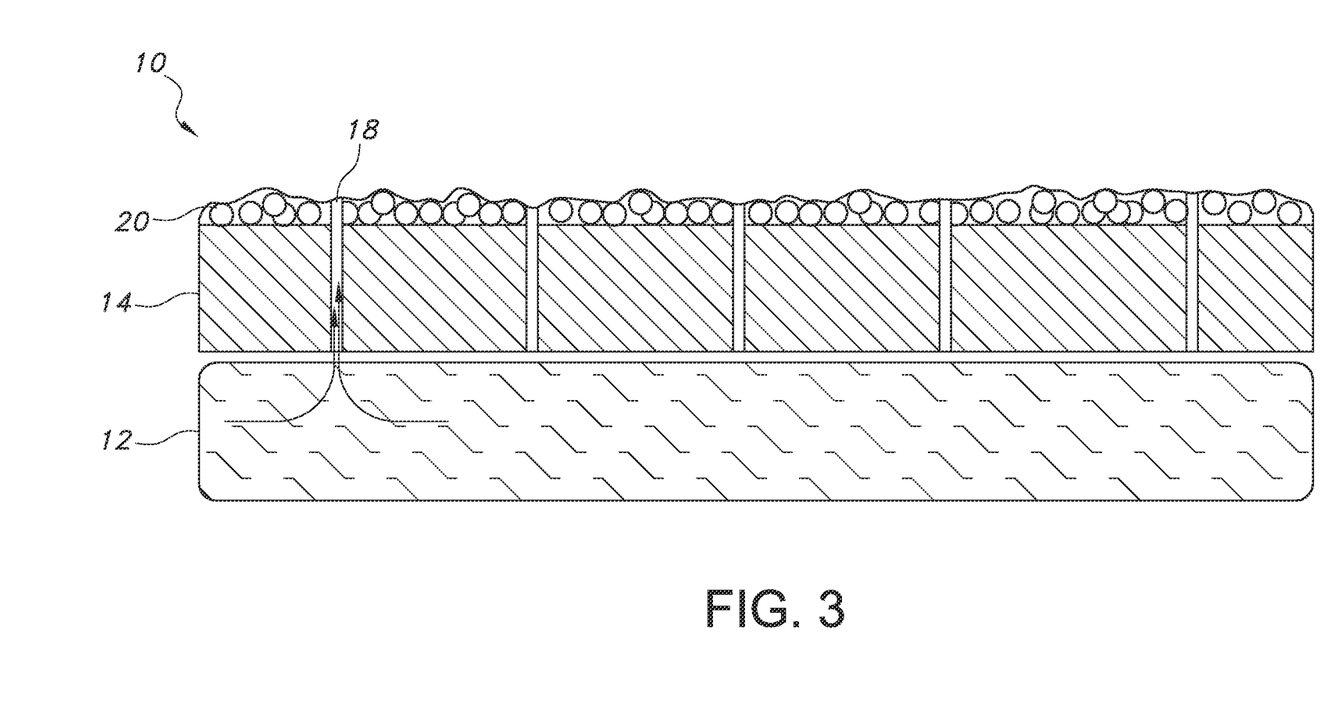
FIG. 3 illustrates a schematic cross-sectional view of one embodiment of a dressing construction according to the present disclosure, particularly illustrating a dressing with two layers having pores configured therein to assist with liquid movement through the layers, wherein the lower layer is in contact with the wound and the upper layer is in liquid communication with the lower layer, and wherein the upper layer includes a particulate polymer dispersed in a hydrogel that is coated onto the lower layer of the dressing.

The lower layer of Example 1 was used. The upper layer includes a coating of polyacrylate powder (Aquasorb 3005 KC, from SNF Inc.) dispersed into a hydrogel and then coated onto the wound dressing. Exemplary hydrogel coating formulations include carboxymethylcellulose, hydroxyethylcellulose, hydroxypropylcellulose, carbomer, polyvinylpyrolidone, polyethylene glycol, alginates, xanthan gum, scleroglycan gum, or similar in the concentration range of 0.1% to 5% wt/wt. In this example, carboxymethylcellulose was used at a 2% concentration. The formulation also contained a humectant, examples, of which include glycerin or propylene glycol in the range of 0.5% to 20% wt/wt. Glycerin was used in this example at a concentration of 10%, e.g. to add flexibility to the coating). The formulation also contains a powdered superabsorbent polymer or copolymer with particle size ranging from 10 micrometers (um) to 500 um and at a concentration of 0.1% to 20% wt/wt. The material used was Aquasorb® 3005 KC from SNF Inc. and the concentration was 2.2%. The remainder of the formulation contained a polar solvent, examples of which are water, an alcohol or acetone. In this example, water was used. The coating can be applied to the substrate by slot coating, Meyer rod, or similar technique familiar to those skilled in coating technologies. The coating in this example was applied using a Meyer rod. The coating solvent was evaporated by applying heat. For example, in this example, the solvent (e.g. water) was evaporated in a drying oven at 55° C. for about 2 hours. The weight of the starting lower layer was approximately 1.5 grams before the coating was added. Approximately 3 grams of the coating formulation was applied to the substrate. After the solvent was evaporated, the overall structure, including both layers weighed about 2 grams. Pore structures were perforated into the device to the desired pore density as in Example 1. A schematic cross-sectional drawing of this construction is shown in FIG. 3, wherein the wound the dressing 10 is placed on the wound 12. Further, as shown, the wound dressing 10 has two layers, with the lower layer 14 being in contact with the wound 12 and the upper layer 20 having superabsorbent dispersed in a hydrogel. In addition, as shown, the wound dressing 10 includes a plurality of pores 18 configured through the layers, 14, 20.

Example 3

In this embodiment, instead of coating the high-absorbing upper layer onto the lower, less absorbing, layer, the upper layer was made separately and then glued onto the lower layer. The lower layer was produced utilizing the polymer blend formulation described on Example 1 which contains a monomer to crosslinker ratio of (180:1). The upper layer was produced in a similar manner except that the formulation was altered to include less crosslinker, in this case a monomer to crosslinker ratio of 300:1, which produces a higher absorptive capacity. The two layers were placed in contact with one another and attached with an adhesive, examples of which are cyanoacrylate and polyurethane based adhesive. The cyanoacrylate was used in this example. The pores were perforated into the 2-layer structure as in Example 1 to aid in the wicking of fluid into the upper layer of the dressing.

Example 4

The lower layer of the dressing (again from Example 1) was composed of a non-ionic crosslinked polyacrylamide of example 1 at approximately 45% wt/wt basis blended with glycerin also at approximately 45% wt/wt, as well as about 5% guar gum and approximately 5% of excipients. The upper layer was fine, open celled Kendall™ polyurethane foam dressing, but it could be replaced by any soft hydrophilic foam. It was held onto the first layer using a cyanoacrylate adhesive. The adhesive was roll coated onto the lower substrate layer. Pores were then added to the structure as in Example 1.

Example 5

In this example, the lower layer is synthesized by combining 535 grams of water with 0.285 grams of bisacrylamide. Once dissolved, 29.2 grams of acrylamide is added followed by the addition of a slurry which consists of 29.56 grams of glycerin and 3.23 grams of guar gum. Sodium chloride is added (0.57 grams) followed by 0.1173 grams of silver nitrate. In order to initiate the polymerization, 0.2 grams of tetramethylethylenediamine (TEMED) is added followed by 0.2 grams of ammonium persulfate. Once the mixing is complete, the liquid is then transferred into a mold where it is allowed to polymerize for about 2 to about 24 hours.

In a separate container/mixing vessel, the upper layer is synthesized by combining 537 grams of water with 0.112 grams of bisacrylamide. Once dissolved 29.2 grams of acrylamide is added followed by the addition of a slurry which consists of 29.56 grams of glycerin and 3.24 grams of guar gum. Sodium chloride is added (0.57 grams) followed by 0.1173 grams of silver nitrate. In order to initiate the polymerization 0.2 grams of tetramethylethylenediamine (TEMED) is added followed by 0.1410 grams of ammonium persulfate. Once the mixing is complete the liquid is then transferred into a mold where it is allowed to polymerize for about 2 to about 24 hours.

Once the polymerization step is complete, the polymer gel sheets are then removed from their respective molds. The upper and lower gel formulations are placed in contact with each other such that one is on top of the other. The layered gel is then placed in an oven to dry at about 50° C. to about 60° C. for approximately 18 hours. Once the drying is complete, the dehydrated gel layers are now adhered to each other and are not easily separated. At this point, the perforations can be made through the layers using any suitable method. For example as mentioned, the perforations can be made using a punch or any other type of puncturing device, which provides the desired fluid transfer through the layers. The dehydrated sheets may be rehydrated slightly to increase pliability and/or cut to the desired final shape.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims.

What is claimed is:

1. A wound dressing for covering a wound of a patient, comprising:
a wound-contacting lower layer having a first liquid absorption rate and a first degree of crosslinking, the lower layer comprising one or more lower perforations configured therethrough; and
an upper layer configured adjacent to the lower layer, the upper layer comprising one or more upper perforations configured therethrough and aligning with the one or more lower perforations, the upper layer being in liquid communication with the lower layer via the aligned one or more upper perforations and the one or more lower perforations, the upper layer having a second liquid absorption rate, the upper layer comprising a superabsorbent polymer having a second degree of crosslinking, the second liquid absorption rate being higher than the first liquid absorption rate, the second degree of crosslinking of the upper layer being lower than the first degree of crosslinking of the lower layer.

2. The wound dressing of claim 1, wherein the one or more lower and upper perforations comprise at least one of pores, channels, or slits.

3. The wound dressing of claim 1, wherein the superabsorbent polymer of the upper layer is dispersed in a hydrogel.

4. The wound dressing of claim 1, wherein the upper layer comprises an absorbent foam, the foam comprising a liquid absorption rate that is higher than the first liquid absorption rate the lower layer.

5. The wound dressing of claim 1, wherein liquid communication is provided by physical contact between the layers.

6. The wound dressing of claim 1, wherein at least one of the lower layer or the upper layer further comprises one or more additives.

7. The wound dressing of claim 6, wherein the one or more additives comprise at least one of silver salts, silver nanoparticles, silver sulfadiazine, bacitracin, neomycin, polymyxin b, sulfacetamide sodium, sulfur, quaternary ammonium compounds, or povidone iodine.

8. The wound dressing of claim 1, wherein at least one of the lower layer or the upper layer further comprises agents to promote wound healing, the agents comprising at least one of oxygen, nitrogen oxide, growth factors, vitamin C, vitamin E, aloe, or combinations thereof.

9. The wound dressing of claim 1, wherein at least one of the lower layer or the upper layer further comprises one or more debriding agents, the one or more debriding agents comprises at least one of papain, honey, trypsin, collagenase, urea, or combinations thereof.

10. A wound dressing for covering a wound of a patient, comprising:
- a wound-contacting lower layer having a first liquid absorption rate and a first degree of crosslinking, the lower layer comprising one or more lower perforations configured therethrough; and
- an upper layer configured adjacent to the lower layer and facing away from the patient, the upper layer comprising one or more upper perforations configured therethrough and aligning with the one or more lower perforations, the upper layer being in liquid communication with the lower layer via the aligned one or more lower perforations configured in the lower layer and the one or more upper perforations configured in the upper layer, the upper layer having a second liquid absorption rate, the upper layer comprising a superabsorbent polymer having a second degree of crosslinking, the second liquid absorption rate being higher than the first liquid absorption rate, the second degree of crosslinking of the upper layer being lower than the first degree of crosslinking of the lower layer.

11. The wound dressing of claim 10, wherein the lower layer comprises a superabsorbent polymer having a predetermined degree of crosslinking.

12. The wound dressing of claim 11, wherein the one or more lower and upper perforations comprise at least one of pores, channels, or slits.

13. The wound dressing of claim 10, wherein the upper layer comprises an absorbent foam, the foam comprising a liquid absorption rate that is higher than the first liquid absorption rate the lower layer.

14. The wound dressing of claim 10, wherein liquid communication is further provided by physical contact between the layers.

15. The wound dressing of claim 10, wherein at least one of the lower layer or the upper layer further comprises one or more additives, wherein the one or more additives comprise at least one of silver salts, silver nanoparticles, silver sulfadiazine, bacitracin, neomycin, polymyxin b, sulfacetamide sodium, sulfur, quaternary ammonium compounds, or povidone iodine.

* * * * *